(12) United States Patent
Yonce et al.

(10) Patent No.: US 8,509,897 B2
(45) Date of Patent: Aug. 13, 2013

(54) MORPHOLOGY-BASED DIAGNOSTIC MONITORING OF ELECTROGRAMS BY IMPLANTABLE CARDIAC DEVICE

(75) Inventors: David J. Yonce, Fridley, MN (US); David Ternes, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1916 days.

(21) Appl. No.: 10/723,254

(22) Filed: Nov. 26, 2003

(65) Prior Publication Data
US 2004/0158165 A1    Aug. 12, 2004

Related U.S. Application Data

(63) Continuation-in-part of application No. 10/251,629, filed on Sep. 19, 2002, now Pat. No. 7,286,876.

(51) Int. Cl.
*A61N 1/372* (2006.01)

(52) U.S. Cl.
CPC .................................. *A61N 1/37217* (2013.01)
USPC .......................................................... 607/28

(58) Field of Classification Search
USPC ................. 600/373, 374, 393, 508, 509, 510, 600/516, 519, 521, 523; 607/4, 5, 9, 27, 607/28, 116, 119
See application file for complete search history.

(56) References Cited

U.S. PATENT DOCUMENTS

| | | | |
|---|---|---|---|
| 4,832,041 A | 5/1989 | Wang et al. | |
| 5,273,049 A | 12/1993 | Steinhaus et al. | |
| 5,312,445 A | 5/1994 | Nappholz et al. | |
| 5,331,966 A | 7/1994 | Bennett et al. | |
| 5,391,192 A | 2/1995 | Lu et al. | |
| 5,431,691 A * | 7/1995 | Snell et al. ...................... | 607/27 |
| 5,660,184 A | 8/1997 | Donehoo et al. | |
| 5,674,254 A | 10/1997 | van Krieken | |
| 5,755,739 A | 5/1998 | Sun et al. | |
| 5,771,898 A | 6/1998 | Marinello | |
| 5,778,881 A | 7/1998 | Sun et al. | |
| 5,782,888 A | 7/1998 | Sun et al. | |
| 5,830,150 A * | 11/1998 | Palmer et al. .................. | 600/523 |
| 6,101,416 A | 8/2000 | Sloman | |
| 6,169,921 B1 | 1/2001 | KenKnight et al. | |
| 6,253,102 B1 | 6/2001 | Hsu et al. | |

(Continued)

FOREIGN PATENT DOCUMENTS

| WO | WO-03/020366 A1 | 3/2003 |
|---|---|---|
| WO | WO-03/037428 A2 | 5/2003 |
| WO | WO-2004/026398 A1 | 4/2004 |

OTHER PUBLICATIONS

"International Search Report for corresponding PCT Application No. PCT/US2004/039457", (Apr. 12, 2005), 4 pgs.

*Primary Examiner* — Christopher D Koharski
*Assistant Examiner* — Frances Oropeza
(74) *Attorney, Agent, or Firm* — Schwegman Lundberg & Woessner, P.A.

(57) ABSTRACT

A system and method is presented in which an implantable cardiac device is configured to generate representative electrograms which can be transmitted to an external programmer for display. A representative electrogram represents a patient's typical electrogram during a defined time period or when a particular condition exists. Such representative electrograms may be averages or other statistical measures of electrograms recorded continuously or periodically during the defined time period or during the time when the particular condition exists.

12 Claims, 5 Drawing Sheets

(56) References Cited

U.S. PATENT DOCUMENTS

| | | |
|---|---|---|
| 6,418,340 B1 * | 7/2002 | Conley et al. .................. 600/523 |
| 6,609,023 B1 | 8/2003 | Fischell et al. |
| 6,748,274 B2 * | 6/2004 | Levine et al. ................... 607/32 |
| 7,050,857 B2 * | 5/2006 | Samuelsson et al. ........... 607/60 |
| 2002/0193696 A1 | 12/2002 | Hsu et al. |
| 2003/0083711 A1 | 5/2003 | Yonce et al. |
| 2004/0158165 A1 | 8/2004 | Yonce et al. |

* cited by examiner

MORPHOLOGY-BASED DIAGNOSTIC MONITORING OF ELECTROGRAMS BY IMPLANTABLE CARDIAC DEVICE

RELATED APPLICATIONS

This application is a continuation-in-part of U.S. patent application Ser. No. 10/251,629, filed on Sep. 19, 2002, now issued as U.S. Pat. No. 7,286,876, the disclosure of which is hereby incorporated by reference (referred to herein as the '629 application).

FIELD OF THE INVENTION

This invention pertains to implantable cardiac devices such as cardiac pacemakers and, in particular, to systems and methods for monitoring a patient's clinical condition.

BACKGROUND

Implantable cardiac devices are commonplace today, particularly for treating cardiac rhythm dysfunction. Cardiac pacemakers, for example, are implantable medical devices that delivering electrical pacing pulses to the heart in order to treat bradycardia (a heart rate that is too slow) due to either chronotropic incompetence or a conduction system defect or to treat tachycardia (a heart rate that is too fast). Implantable cardioverter/defibrillators (ICD's) are devices that deliver electrical energy to the heart in order to reverse excessively rapid heart rates including life threatening cardiac arrhythmias such as ventricular fibrillation. Since some patients have conditions that necessitate pacing and also render them vulnerable to life-threatening arrhythmias, implantable cardiac devices have been developed that combine both functions in a single device. Also included within the concept of cardiac rhythm is the manner and degree to which the heart chambers contract during a cardiac cycle to result in the efficient pumping of blood. Patients who exhibit pathology of conduction pathways, such as bundle branch blocks, can suffer compromised cardiac output. In order to treat these problems, pacemakers have been developed which provide electrical pacing stimulation to one or both of the atria and/or ventricles during a cardiac cycle in an attempt to improve the coordination of atrial and/or ventricular contractions, termed cardiac resynchronization therapy.

Most pacemakers today are operated in some sort of synchronous mode where the pacing pulses are delivered in a manner that is dependent upon the intrinsic depolarizations of the heart as sensed by the pacemaker. ICD's must also sense the electrical activity of the heart in order to detect an arrhythmia that will trigger delivery of the shock pulse in an attempt to reverse the condition. Such sensed information can also be stored by the device and transferred later to an external programmer via a radio link. The present invention is concerned with a method and system by which an implantable cardiac device may store data representing the electrical activity of the heart for display by an external programmer or other apparatus in a clinically useful manner.

SUMMARY OF THE INVENTION

In accordance with the invention, an implantable cardiac device is configured to generate representative electrograms which can be transmitted to an external programmer for display, where a representative electrogram represents a patient's typical electrogram during a defined time period or when a particular condition exists. Such representative electrograms may be averages or other statistical measures of electrograms recorded continuously or periodically during the defined time period or during the time when the particular condition exists. The recorded electrograms may be constrained to constitute either paced or intrinsic beats, or separate representative electrograms may be generated for representing both intrinsic and paced beats.

In one embodiment, representative electrograms are generated for each of a plurality of discrete time intervals over some long-term period of time, where the discrete time intervals may be contiguous or separated by constant or varying periods of time. In order to eliminate the variability of electrogram morphology with heart rate, the electrograms used to compute the representative electrogram for a particular time interval may be constrained to be recorded only when the patient's heart rate is within a specified range. An aggregate of such representative electrograms may then be displayed by an external programmer in graphical form as indexed by time. In another embodiment, representative electrograms are generated where each such electrogram represents the patient's typical electrogram when the heart rate is in a particular range. An aggregate of such representative electrograms may then be displayed by an external programmer in graphical form as indexed by heart rate. In each of these embodiments, the graphical display enables a clinician to easily ascertain changes in electrogram morphology by visual inspection and thus monitor the patient's clinical status as reflected by morphology changes in the patient's electrogram waveform.

DETAILED DESCRIPTION

Figure 1:
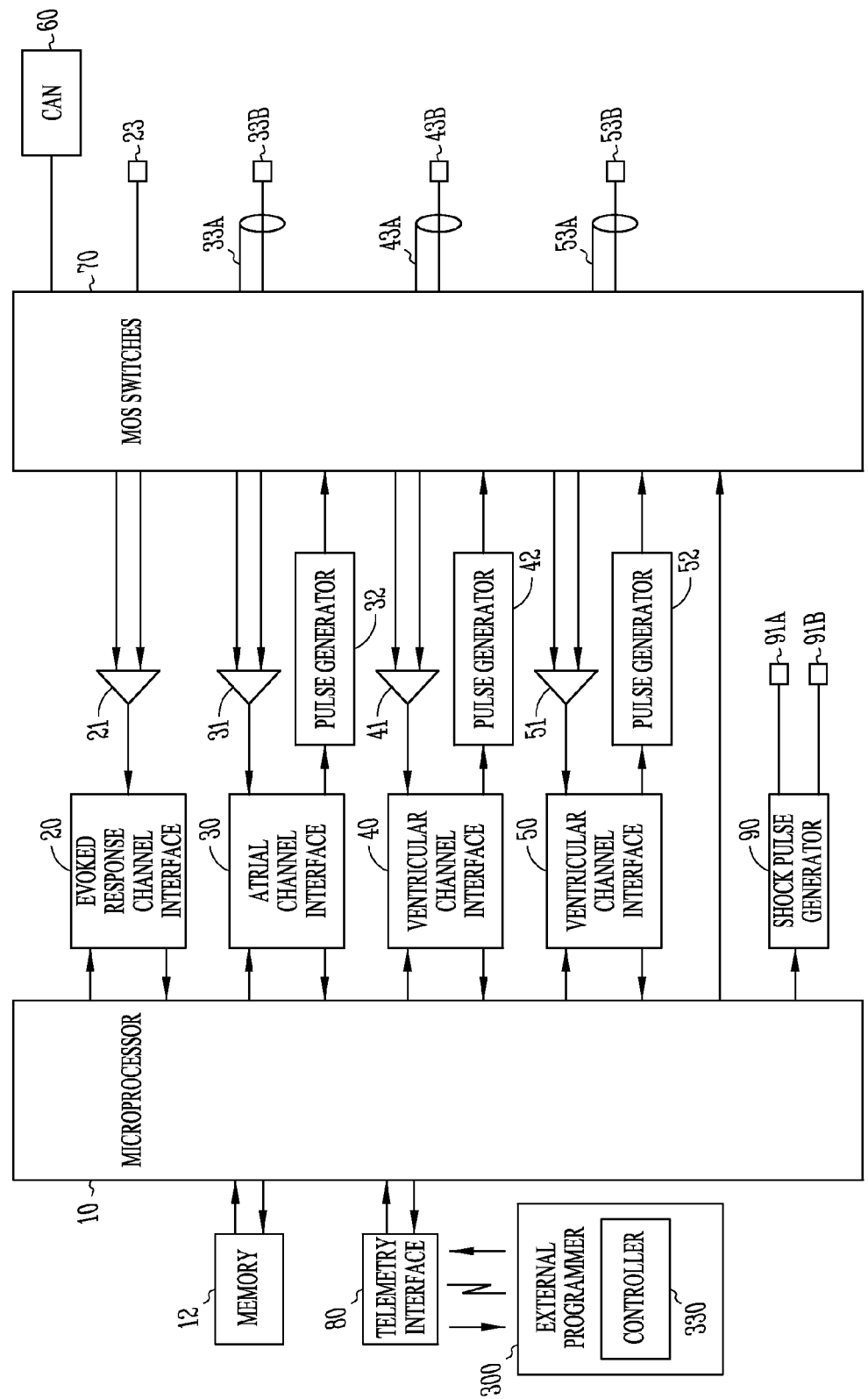
FIG. 1 is a block diagram of a multi-site pacemaker.

The voltage signal produced by a sensing electrode of an implantable cardiac device while sensing cardiac electrical activity is referred to as an electrogram signal. An electrogram signal is analogous to a surface ECG and provides a temporal record of the cardiac depolarization and repolarization that occurs during either an intrinsic or a paced beat. The sensing circuitry of the device generates a chamber sense (i.e., an atrial or ventricular sense) when the electrogram signal of a particular channel exceed a specified threshold. A ventricular sense would correspond to an R wave on an ECG, and an atrial sense would correspond to a P wave. A cardiac rhythm management device may interpret chamber sense signals in order to detect arrhythmias and/or to control the delivery of paces in accordance with a pacing algorithm that employs such senses to trigger or inhibit pacing. Electrogram signals can also be digitized and recorded by an implantable cardiac device and then either transmitted via a telemetry link to an external programmer or stored for later transmission. The patient's cardiac activity may thus be observed in real-time or over a selected historical period for diagnostic purposes.

An electrogram generated by a pair of electrodes spaced apart sufficiently to be able to follow a wave of depolarization or repolarization as it travels over a relatively large volume of the myocardium may be referred to as a wide-vector electrogram. The waveform morphology of a wide-vector electrogram is the result of the summation of the electrical activity of millions of myocardial cells. The manner and time course of myocardial depolarization or repolarization is determined by both the myocardial substrate and the concentrations of ions in the extra-cellular fluid. Changes to either of these factors in an individual patient as a result of things related to the patient's health status such as myocardial remodeling in response to some degree of heart failure, a change in drug regimen, a change in fitness, myocardial ischemia, or myocardial infarction are reflected as changes in the morphology of the wide-vector electrogram. An electrogram which is not a wide-vector electrogram (as recorded by from a bipolar lead with closely-spaced electrodes, for example) may also reflect such changes, although perhaps not as robustly as the wide-vector electrogram. In either case, however, stochastic variability in electrogram morphology may make it difficult to determine whether a change in electrogram morphology as detected by comparing a single electrogram with a reference electrogram is due to natural variability or due to an actual change in the patient's health status. If a number of representative electrograms taken over time are displayed as an aggregate, however, a progressive change in the patient's health status may be revealed as trending changes in electrogram waveform morphology which can more easily be detected. Detection of changes in electrogram morphology may provide insight into the gradual improvement or degradation of a patient's heart function which can then be used to determine the effectiveness of various therapies and may also provide insight into abrupt changes to the patient's heart function that can be correlated to an event such as a heart attack or arrhythmic episode.

Representative electrograms can also be obtained with respect to a parameter other than time to reveal trending morphology changes with respect to that parameter. Such a parameter may be a measurable physiological parameter with which electrogram morphology is expected to vary such as heart rate. Certain changes in health status may cause changes in the way that the electrogram morphology varies with heart rate, and such changes may be revealed by an aggregate display of representative electrograms obtained with respect to heart rate. Detection of such changes may provide insight into abnormalities of heart function such as rate dependent left bundle branch block or chronotropic incompetence. Detection of changes in the morphology of evoked response electrograms acquired with respect to pacing rate may provide insight into how the effectiveness of various programmed pacing parameters varies with rate.

Further elimination of natural variability in electrogram morphology (which may be regarded as noise for purposes of morphology analysis) may be obtained by averaging a number of recorded electrograms to obtain each representative electrogram. For example, in the case of representative electrograms with respect to heart rate, representative electrograms can be obtained for each of a plurality of discrete heart rate ranges with each representative electrogram being an average of electrograms recorded when the patient's heart rate was within the particular range. Similarly, in the case of representative electrograms with respect to time, representative electrograms can be obtained for each of a plurality of discrete time intervals with each representative electrogram being an average of electrograms recorded during the discrete time interval. It may also be desirable to eliminate the variability in the morphology of representative electrograms with respect to time which is due to heart rate by deriving the representative electrograms only from electrograms recorded when the heart rate is within a specified range.

In accordance with the present invention, an implantable cardiac device configured with one or more sensing channels and associated circuitry for recording and storing electrograms is programmed to generate representative electrograms with respect to time and/or with respect to heart rate. A representative electrogram may be a single electrogram recorded during at a specified time or when the heart rate is within a specified range or may be an average of electrograms recorded during a discrete time interval or when the heart rate is within a specified range. Averages may be computed as moving averages of electrograms recorded either continuously or periodically during a discrete time interval or when the heart rate is within a specified range. The representative electrograms may reflect either intrinsic or paced cardiac electrical activity, or separate representative electrograms may be derived from intrinsic and paced beats. A set of representative electrograms may be downloaded to an external programmer (or other external device) which can then graphically display the downloaded representative electrograms as an aggregate indexed with respect to time or heart rate.

Set forth below is a description of the hardware components of an exemplary system for practicing the invention as just described. Particular embodiments of algorithms for the acquisition of representative electrograms by the implantable device are also described along with examples of their graphical display.

a. Exemplary Hardware Platform

The present invention may be incorporated into any cardiac device with the capability of sensing cardiac electrical activity, including devices for monitoring only and those for delivering therapy in the form of electrical stimulation to the heart. For illustrative purposes, however, a the invention will be described with reference to a dual-chamber pacemaker (i.e., one that senses and/or paces both the atria and ventricles) having two ventricular pacing channels for pacing both ventricles or delivering two paces to a single ventricle as shown in FIG. 1. (As the term is used herein, a pacemaker is any cardiac rhythm management device with a pacing functionality regardless of any additional functions it may perform such as cardioversion/defibrillation.) Such a device may collect electrograms from either intrinsic or paced cardiac activity, the latter being referred to as evoked response electrograms, and derive representative electrograms therefrom. Also, as described below, having two ventricular sensing channels allows the device to align intrinsic electrograms recorded from one such channel with respect to ventricular senses detected in the other channel so that the recorded electrograms all start from a constant reference point.

Cardiac rhythm management devices are typically implanted subcutaneously on a patient's chest and have leads threaded intravenously into the heart to connect the device to electrodes used for sensing and pacing. A programmable electronic controller causes the pacing pulses to be output in response to lapsed time intervals and sensed electrical activity (i.e., intrinsic heart beats not as a result of a pacing pulse). The device senses intrinsic cardiac electrical activity by means of internal electrodes disposed near the chamber to be sensed. A depolarization wave associated with an intrinsic contraction of the atria or ventricles that is detected by the pacemaker is referred to as an atrial sense or ventricular sense, respectively. In order to cause such a contraction in the absence of an intrinsic beat, a pacing pulse (either an atrial pace or a ventricular pace) with energy above the capture threshold must be delivered to the chamber.

The controller of the device is made up of a microprocessor 10 communicating with a memory 12, where the memory 12 may comprise a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. The controller is capable of operating the pacemaker in a number of programmed modes where a programmed mode defines how pacing pulses are output in response to sensed events and expiration of time intervals. A telemetry interface 80 is provided for communicating with an external programmer 300. The external programmer is a computerized device with a controller 330 and display screen 350 that can interrogate the device and receive stored data as well as adjust the device's operating parameters.

The embodiment shown in FIG. 1 is equipped with multiple sensing/pacing channels, where a pacing channel is made up of a pulse generator connected to an electrode while a sensing channel is made up of the sense amplifier connected to an electrode. A MOS switching network 70 controlled by the microprocessor is used to switch the electrodes from the input of a sense amplifier to the output of a pulse generator. The switching network 70 also allows the sensing and pacing channels to be configured by the controller with different combinations of the available electrodes. The channels may be configured as either atrial or ventricular channels allowing the device to deliver conventional ventricular single-site pacing with or without atrial tracking, biventricular pacing, or multi-site pacing of a single chamber. In an example configuration, an atrial sensing/pacing channel comprises ring electrode 33a, tip electrode 33b, sense amplifier 31, pulse generator 32, and an atrial channel interface 30 which communicates bidirectionally with a port of microprocessor 10. The device also has two ventricular sensing/pacing channels that similarly include ring electrodes 43a and 53a, tip electrodes 43b and 53b, sense amplifiers 41 and 51, pulse generators 42 and 52, and ventricular channel interfaces 40 and 50. The device also has an evoked response sensing channel that comprises an evoked response channel interface 20 and a sense amplifier 21 that has its differential inputs connected to a unipolar lead 23 and to the device housing or can 60 through the switching network 70. The evoked response sensing channel may be used to verify that a pacing pulse has achieved capture of the heart in a conventional manner or, as explained below, used to record an evoked response or intrinsic electrogram. A shock channel is also provided comprising a shock pulse generator 90 and shock electrodes 91a and 91b that enables the device to deliver a defibrillation shock to the heart when fibrillation or other tachyarrhythmia is detected. Evoked response or intrinsic electrograms may also be generated by the shock channel wherein one or both of the shock leads normally used for delivering defibrillation shocks to the heart is switched to a sensing amplifier by the switch matrix 70.

The channel interfaces communicate bi-directionally with a port of microprocessor 10 and include analog-to-digital converters for digitizing sensing signal inputs from the sensing amplifiers, registers that can be written to for adjusting the gain and threshold values of the sensing amplifiers, and registers for controlling the output of pacing pulses and/or changing the pacing pulse amplitude. In this embodiment, the device is equipped with bipolar leads that include two electrodes which are used for outputting a pacing pulse and/or sensing intrinsic activity. Other embodiments may employ unipolar leads with single electrodes for sensing and pacing.

The switching network 70 may also configure a channel for unipolar sensing or pacing by referencing an electrode of a unipolar or bipolar lead with the device housing or can 60. For analysis of waveform morphology, it is preferable to record an electrogram with a unipolar electrode that "sees" a larger volume of the myocardium as a wave of electrical activity spreads than does a bipolar electrode. A convenient electrode for this purpose is the shock electrode that the device normally uses for delivering cardioversion/defibrillation shocks. The shock channel incorporating the shock electrode may thus be used to generate electrograms for recording and subsequent generation of representative electrograms for morphology analysis. In order to ensure that all recorded shock channel electrograms start from the same temporal reference point, the shock channel (or other unipolar channel) electrograms may be aligned with a bipolar electrogram simultaneously recorded from a sensing channel normally used to sense R waves for rate determination, referred to as the rate channel. The shock channel electrograms may be aligned with respect to a selected alignment point of the rate channel electrogram (e.g., the peak amplitude of the QRS complex).

The controller 10 controls the overall operation of the device in accordance with programmed instructions stored in memory. The controller 10 interprets electrogram signals from the sensing channels and controls the delivery of paces in accordance with a pacing mode. The sensing circuitry of the pacemaker generates atrial and ventricular electrogram signals from the voltages sensed by the electrodes of a particular channel. When an electrogram signal in an atrial or ventricular sensing channel exceeds a specified threshold, the controller detects an atrial or ventricular sense, respectively, which pacing algorithms may employ to trigger or inhibit pacing. The electrogram signals from any of the sensing channels of the pacemaker in FIG. 1 can also be digitized and recorded by the controller in order to generate representative electrograms.

b. Acquisition and Display of Representative Electrograms

In accordance with the invention, an implantable cardiac rhythm management device with the capability of recording and processing electrograms is programmed to compute representative electrograms with respect to defined time periods or particular heart rates. Such representative electrograms may then be downloaded to an external programmer for display. The representative electrograms may be displayed in an aggregate fashion with the time period or heart rate represented by the individual representative electrograms indicated graphically. The following are descriptions of two example embodiments.

Figure 2A:
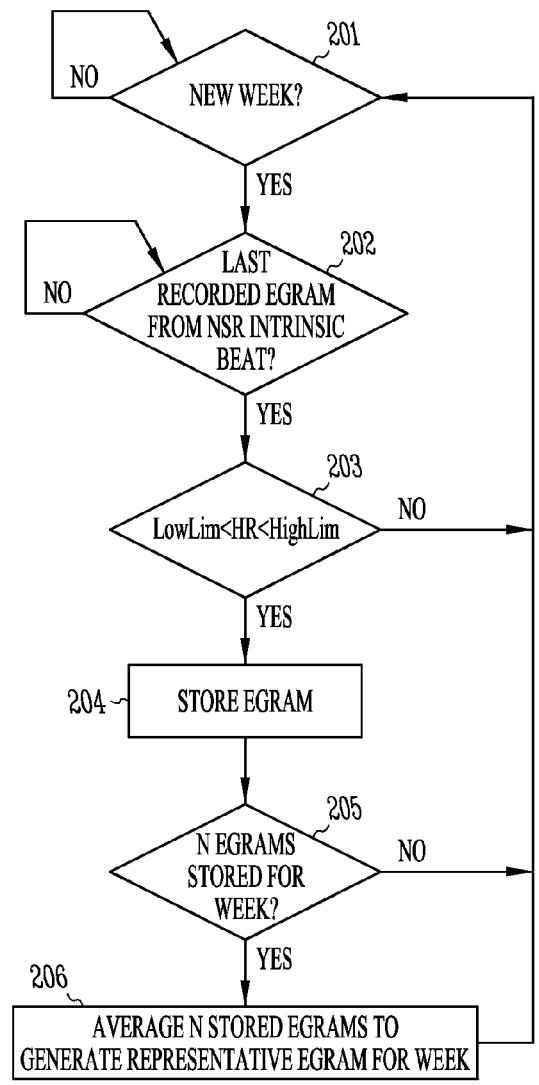
FIG. 2A illustrates an exemplary algorithm for acquiring representative electrograms with respect to time.

FIG. 2A illustrates an exemplary algorithm for collecting representative electrograms with respect to time as could be performed by an appropriately programmed implantable device. In different example embodiments, representative electrograms may be obtained on an hourly, daily, and/or weekly basis for representing those time periods. In this example, representative electrograms are computed on a weekly basis. At step 201, the device waits until a new week begins for which a representative electrogram has not yet been computed. The device records an electrogram during each cardiac cycle and either stores or discards the data. At step 202, the device determines whether the last recorded electrogram was an intrinsic or paced beat. Representative electrograms may be computed to represent either intrinsic or paced cardiac activity. In this embodiment, however, weekly representative electrograms are generated only for intrinsic beats. If the last beat was a normal sinus rhythm beat (e.g., not an ectopic beat), the device at step 203 checks the RR interval to determine if the heart rate for that beat was within a specified range defined by a high limit value HighLim and a low limit value LowLim. If so, the electrogram is stored at step 204 for later averaging. At step 205, the device loops back to step 202 until N electrograms have been stored, where N is a programmable parameter which specifies how many electrograms are to be averaged in order to generate a representative electrogram. At step 206, the N electrograms are averaged to compute a representative electrogram for the week which is then stored. The process may compute weekly representative electrograms on a continuous basis with only a specified number of the most recent representative electrograms maintained in memory with the oldest representative electrograms being discarded.

Figure 2B:
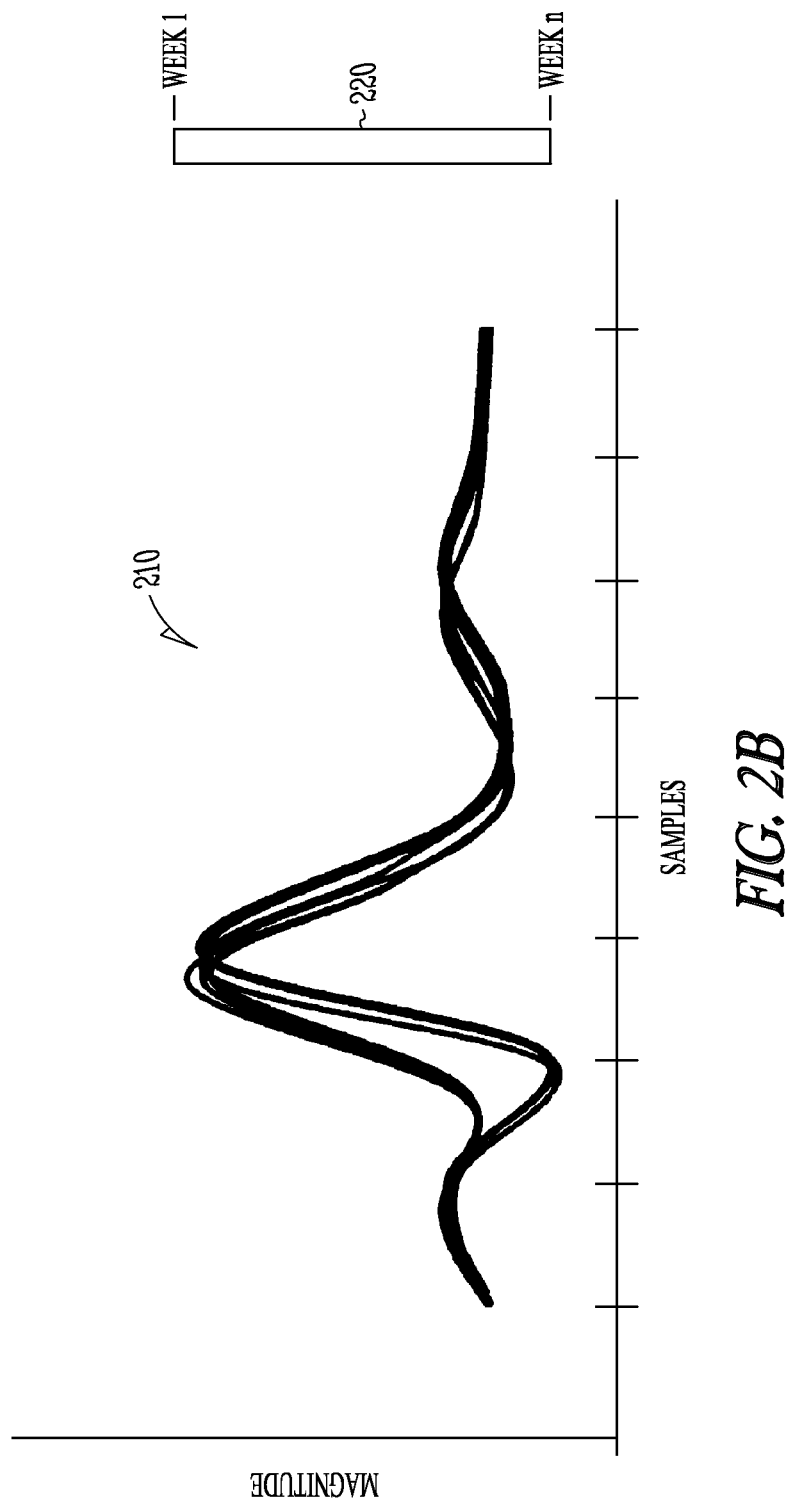
FIG. 2B depicts an aggregate display of representative electrograms acquired with respect to time.

FIG. 2B shows an example of an aggregate display of the weekly representative electrograms. Such a display may be generated by the external programmer either in the form of a printout or an image on the display screen of the programmer. Representative electrograms for each of weeks numbered 1 through n are displayed with magnitude plotted versus time or sample number. Each of the electrograms 210 are shaded or colored according to the week which the electrogram represents. A legend 220 indicates the colors or shades which correspond to the weeks numbered 1 through n. In different example embodiments, the system may allow the user to select specific weeks for which representative electrograms are displayed or to select all weeks since the last reset.

Figure 3A:
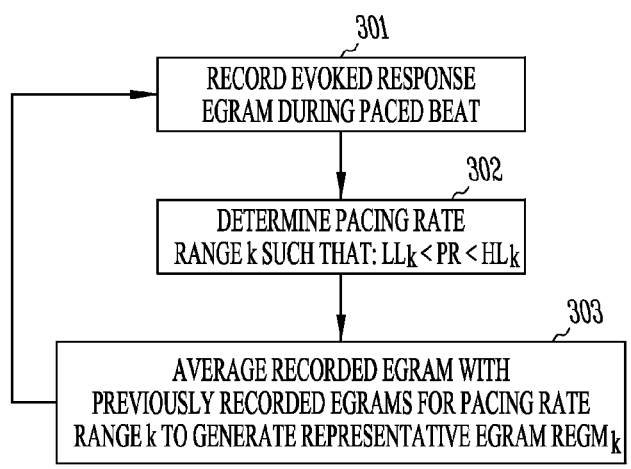
FIG. 3A illustrates an exemplary algorithm for acquiring representative electrograms with respect to heart rate.

FIG. 3A illustrates an exemplary algorithm for acquiring representative evoked response electrograms for a plurality of different pacing rates. The algorithm enables the device to opportunistically acquire such representative electrograms as the pacing rate varies during normal operation. In different example embodiments, the implantable device acquires the representative electrograms over the lifetime of the device, at a particular time (e.g., during a prescribed exercise test period), or according to a particular schedule. Referring to FIG. 3A, specified number M of different pacing rate ranges are indexed by an integer k for k=1 through M, with each pacing rate range k defined by an upper limit value $UL_k$ and a lower limit value $LL_k$. A particular pacing rate PR then corresponds to a pacing rate range k if it is between the upper and lower limit values which define the range, $UL_k$ and $LL_k$, respectively. At step 301, evoked response electrograms are recorded during paced cardiac cycles on either a continuous or periodic basis. At step 302, after recording an evoked response electrogram, the device compares the current pacing rate PR to the M pairs of upper and lower limit values to determine the current pacing rate range k. At step 303, the recorded electrogram is then stored and averaged with previously recorded electrograms for the pacing rate range k to generate the representative electrogram $REGM_k$ for that pacing rate range.

Figure 3B:
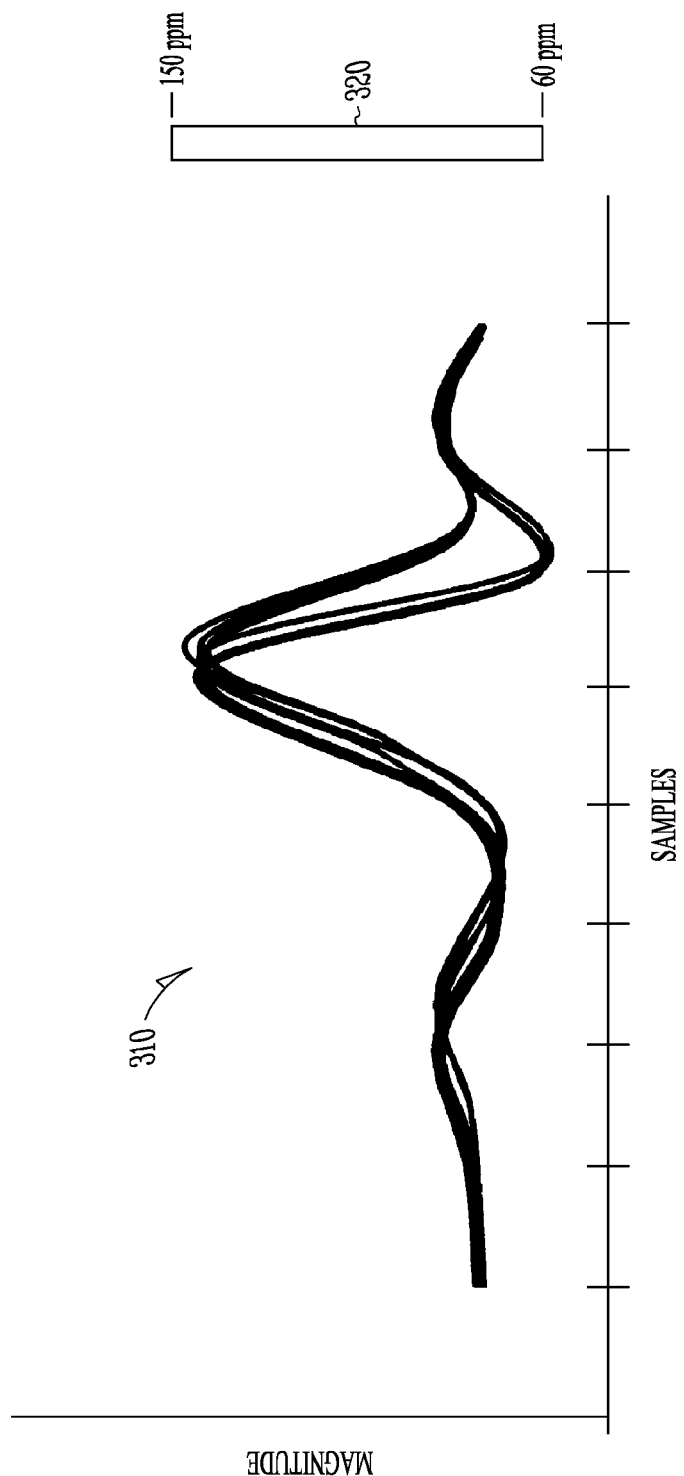
FIG. 3B depicts an aggregate display of representative electrograms acquired with respect to heart rate.

FIG. 3B shows an example aggregate display of the representative electrograms $REGM_k$ for k=1 through M which correspond to the M different pacing rate ranges. Representative electrograms for each pacing rate range are displayed with magnitude plotted versus time or sample number. Each of the electrograms 310 are shaded or colored according to the pacing rate range k which the electrogram represents. A legend 320 indicates the colors or shades which correspond to the different pacing rate ranges where, in this example, the maximum and minimum such ranges correspond to nominal pacing rates of 150 ppm and 60 ppm, respectively. In different example embodiments, the user may ask the system to display all representative electrograms which have been acquired over the lifetime of the device or only those representative electrograms which have been acquired during a specified time period (e.g., during a specific week or since the last reset).

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A system for recording and presenting electrophysiological data, comprising:
   an implantable cardiac device having a first sensing channel for sensing cardiac electrical activity and generating electrogram signals;
   wherein a controller of the implantable cardiac device is programmed to:
   record electrograms over a specified long-term period of time,
   generate representative electrograms for each of a plurality of discrete time intervals within the specified long-term period of time, and
   compute the representative electrogram for each discrete time interval as a time average of electrograms recorded during the discrete time interval only when the patient's heart rate is within a specified range; and,
   an external programmer configured to download representative electrograms from the implantable device and display an aggregate of representative electrograms in graphical form as indexed by time.

2. The system of claim 1 wherein the representative electrograms are intrinsic electrograms.

3. The system of claim 1 wherein the representative electrograms are evoked response electrograms.

4. The system of claim 1 wherein the representative electrograms are displayed on a display screen of the external programmer.

5. The system of claim 1 wherein each of the representative electrograms is displayed as a graph of the electrogram's magnitude with a shading or color of the graph identifying the defined time period represented by the representative electrogram.

6. The system of claim 1 wherein the controller is programmed to continuously generate representative electrograms for consecutive discrete time intervals within the long-term period of time.

7. The system of claim 6 wherein the controller is programmed to maintain a specified number of representative electrograms in memory with the oldest representative electrogram being discarded.

8. A system for recording and presenting electrophysiological data, comprising:
   an implantable cardiac device having a first sensing channel for sensing cardiac electrical activity and generating electrogram signals;
   wherein a controller of the implantable cardiac device is programmed to:
   record electrograms over a specified long-term period of time,
   generate representative electrograms for each of a plurality of heart rate ranges during the specified long-term period of time by computing each representative electrogram for a particular heart rate range as a time average of a plurality of electrograms recorded when a patient's heart rate is within the particular heart rate range, and compute the representative electrogram for a particular heart rate range from one or more electrograms recorded only when the patient's heart rate is within the particular heart rate range; and, an external programmer configured to download representative electrograms from the implantable device and display an aggregate of representative electrograms in graphical form as indexed by the plurality of heart rate ranges.

9. The system of claim 8 wherein the representative electrograms are intrinsic electrograms.

10. The system of claim 8 wherein the representative electrograms are evoked response electrograms and wherein heart rate refers to pacing rate.

11. The system of claim 8 wherein the representative electrograms are displayed on a display screen of the external programmer.

12. The system of claim 8 wherein each of the representative electrograms are displayed as a graph of magnitude versus time or sample number with a shading or color of the graph identifying the defined heart rate range represented by the representative electrogram.

* * * * *